United States Patent [19]

Vrieland et al.

[11] 3,933,932

[45] Jan. 20, 1976

[54] METHOD OF OXYDEHYDROGENATION OF ETHYL BENZENE

[75] Inventors: G. Edwin Vrieland, Midland, Mich.; Hans R. Friedli, Lake Jackson, Tex.

[73] Assignee: The Dow Chemical Company, Midland, Mich.

[22] Filed: May 28, 1974

[21] Appl. No.: 474,126

[52] U.S. Cl............................ 260/669 R; 252/437
[51] Int. Cl.²........................................... C07C 5/48
[58] Field of Search ........ 260/669 R, 680 D, 680 E, 260/683.3; 252/437

[56] References Cited
UNITED STATES PATENTS

| | | | |
|---|---|---|---|
| 3,274,284 | 9/1966 | Karkalits et al................. | 260/680 D |
| 3,308,186 | 3/1967 | Bajars............................ | 260/680 D |
| 3,308,190 | 3/1967 | Bajars............................ | 260/680 D |
| 3,308,197 | 3/1967 | Bajars............................ | 260/680 D |
| 3,733,327 | 5/1973 | Vrieland et al................. | 260/290 V |

*Primary Examiner*—Paul M. Coughlan, Jr.
*Attorney, Agent, or Firm*—Stephen Hoynak; Glwynn R. Baker

[57] ABSTRACT

Lanthanum phosphate, lanthanum pyrophosphate and rare earth phosphates and pyrophosphates containing a major portion of that lanthanum compound are good catalysts for oxydehydrogenating alkyl aromatic compounds, including nitrogen heterocyclics having at least one $C_2$-$C_6$ alkyl side chain to form derivatives having side chain unsaturation. The alkyl aromatic compound can have 1–2 rings. The process is carried out at 450°–640°C. and a space velocity of 55–2500.

7 Claims, No Drawings

3,933,932

METHOD OF OXYDEHYDROGENATION OF ETHYL BENZENE

BACKGROUND OF THE INVENTION

An object of this invention is the provision of a superior catalyst for oxydehydrogenation of an alkyl aromatic compound. Another object is to provide a process for oxydehydrogenating alkyl aromatic compounds in which process superior conversions with high selectivities of the alkyl group to an alkene group are obtained.

SUMMARY OF THE INVENTION

This invention concerns a catalytic method of oxydehydrogenating alkyl aromatic compounds having at least one $C_2$-$C_6$ alkyl group and 1–2 rings in the aromatic moiety, including alkyl substituted nitrogen heterocyclics, to form derivatives having aliphatic unsaturation in the side chain. More particularly, the catalysts are lanthanum phosphate, lanthanum pyrophosphate or rare earth phosphates containing a major portion of lanthanum phosphates and pyrophosphates. The catalyst can also contain small amounts of chromium oxide. The method comprises passing a mixture of an oxygen containing gas, and vapors of the alkyl aromatic compounds, with or without an inert diluent vapor, over the catalyst at a temperature of from about 450°C. to about 650°C., at a space velocity of from about 55 to about 2500.

DETAILED DESCRIPTION OF THE INVENTION

The catalysts used in this invention are prepared by reacting an acidic solution of lanthanum or a rare earth containing a predominant amount of lanthanum with a phosphate in such a ratio that either the phosphate or pyrophosphate of the lanthanum or rare earth is formed.

The molar ratio of oxygen to alkyl aromatic compound can range from about 0.5 to about 4.0 moles of $O_2$ per mole of alkyl aromatic compound, but a preferred range is from about 0.5 to about 1.5 and most preferred is a range of about 0.9 to about 1.1 mole $O_2$ per mole of aromatic compound.

The oxygen can be pure oxygen, air, or air enriched with oxygen.

The space velocity (vol./vol./hr.) can range from about 55 to 2500, but a preferred range is from about 250 to about 1800. Most preferred is a range of from about 800 to about 1800.

Diluents when used can be the noble gases, nitrogen, carbon dioxide or steam. These can range from about 4–16 volumes per volume of alkyl aromatic compound, but preferably range from about 4 to about 11 volumes.

The pressure at which the reaction can be run ranges from 0.5 to about 5 atmospheres, but it is preferable to operate at autogenous pressure which is generally the range of about 1 to about 2 atmospheres.

The reaction can be effected in a temperature range of from about 450°C. to about 650°C., but a preferred range is from about 500°C. to about 650°C.

Care should be exercized to avoid explosive mixtures when feeding the alkyl aromatic compound and oxygen into the reactor.

The examples which follow are intended to illustrate, but not to limit the invention. All parts are by weight unless specifically indicated otherwise.

The reactor for this and subsequent examples was a high silica glass tube 15 mm I.D. and 45 cm. long, with an inlet for the compound to be dehydrogenated and another for a premixed feed of oxygen and an inert diluent. After loading the reactor with catalyst, coarse, high silica chips were placed above the catalyst layer to serve as a mixing and preheating area. The reactor was heated by placing it in an electric resistance furnace.

The reactor was loaded with 20 ml. of the lanthanum or rare earth phosphate or pyrophosphate, and then high silica ships were loaded on top of the catalyst.

The reactor outlet was connected to a valved line which was connected to a vapor phase chromatograph in which $O_2$, $N_2$, CO and $CO_2$ and benzene, toluene alkyl aromatic and alkenyl aromatic hydrocarbons were separated and analyzed. The column for separating the hydrocarbons contained carbowax 20M (2% KOH) on Chromasorb P (60-80M).

EXAMPLE 1

A lanthanum pyrophosphate catalyst was prepared by dissolving 97.8 g. of $La_2O_3$ in 120 ml. of concentrated nitric acid, and diluting to 500 ml. with distilled water. This solution was added slowly, with vigorous stirring, to an aqueous solution containing 114 g. of $NH_4H_2PO_4$ in 500 ml. distilled water and acidified to a pH of 0.9 with nitric acid. The white gelatinous precipitate was dried by heating in an oven at 150°C. for 18 hours, and then gradually raising the oven temperature to 380°C. over a period of 9½ hours. The dried material was crushed and screened. The 8–20 mesh portion was then heated for 2 hours at 550°C. The product contained predominantly $La_4(P_2O_7)_3$, as confirmed by infra-red analysis.

A feed containing a ratio of 6.25:1.04:1 of nitrogen, oxygen and ethyl benzene, respectively, was reacted at 550°C at a GHSV of 241 $hr^{-1}$. The conversion of ethyl benzene was 65.2%, acid selectivity to styrene was 87.9%.

EXAMPLE 2

A rare earth carbonate mixture analyzing 65% lanthanum, 27% of neodymium and 7% praseodymium, as oxides, was used for the preparation of the catalyst. 140 g. of the carbonated mixture were dissolved in 500 ml. of 3.7M nitric acid. The pH was adjusted to 0.9 with ammonium hydroxide and then the rare earth-containing solution was added to an aqueous solution containing 114 g. of $NH_4H_2PO_4$ which had previously been adjusted to a pH of 0.9 with nitric acid.

The precipitate was dried in the manner described in example 1, by periodic increases in temperature up to 550°C. The dried catalyst was crushed and screened. The 8–20 mesh portion was used for oxydehydrogenating ethyl benzene. The catalyst contained a high proportion of pyrophosphates.

The feed ratio of nitrogen, oxygen and ethyl benzene, the reaction temperature and flow rate through the reactor were similar to those described for example 1.

The conversion of ethyl benzene was 66.4% and selectivity to styrene was 86.3%.

EXAMPLE 3

A lanthanum phosphate ($LaPO_4$) catalyst was prepared by dissolving 162.9 g. of $La_2O_3$ in 200 ml. of concentrated nitric acid and diluting to one liter. This solution was added to one liter of a solution containing 205 g. of concentrated $H_3PO_4$. To the combined mixture was slowly added, with rapid stirring, 4.35 liters of 1.5N $NH_4OH$. The final pH was 3. The precipitate was filtered and dried at room temperature over calcium chloride. It was then heated to 550°C. for 4 hours. Infra-red analysis confirmed that the catalyst was predominantly $LaPO_4$.

When tested for its ability to dehydrogenate ethyl benzene, using the ratio of ingredients, the temperature and feed rate described in example 1, it was found that conversion of ethyl benzene was 39.8% and selectivity to styrene was 73.6%.

The data shows that $LaPO_4$ is an effective catalyst for oxydehydrogenating alkyl aromatic compounds to alkenyl aromatic derivatives, but that lanthanum pyrophosphate and the mixed rare earth pyrophosphates whose metal is predominantly lanthanum are superior to the orthophosphate.

We claim:

1. A method of oxydehydrogenating ethyl benzene to styrene comprising feeding a mixture of from about 0.5 to about 4.0 moles of oxygen per mole of ethyl benzene, into admixture with a catalyst consisting essentially of lanthanum phosphate, lanthanum pyrophosphate, a rare earth phosphate having a predominant amount of lanthanum in the metal moiety or a rare earth pyrophosphate having a predominant amount of lanthanum in the metal moiety, at a reaction temperature of from about 450° to about 650°C., and a space velocity of from about 55 to about 2500 and recovering styrene from the effluent.

2. The method of claim 1 in which the reaction temperature is from about 500°C. to about 650°C.

3. The method of claim 1 in which the molar ratio of oxygen is from about 0.5 to 1.5 mols per mol of ethyl benzene.

4. The method of claim 3 in which molar ratio of oxygen is from about 0.9 to about 1.1 per mole of ethyl benzene.

5. The method of claim 1 in which the catalyst is lanthanum pyrophosphate, the feed contains 6.25 volumes of nitrogen and 1.04 volumes of oxygen per volume of vaporized ethyl benzene and the space velocity GSHV is about 240 $hr.^{-1}$.

6. The method of claim 1 in which the catalyst is a rare earth pyrophosphate which has 65% lanthanum, about 27% neodymium and about 7% praseodymium, calculated as oxides, in the metal moiety.

7. The method of claim 1 in which the catalyst is lanthanum phosphate.

* * * * *

UNITED STATES PATENT AND TRADEMARK OFFICE
CERTIFICATE OF CORRECTION

PATENT NO. : 3,933,932
DATED : January 20, 1976
INVENTOR(S) : G. Edwin Vrieland; Hans R. Friedli It is certified that error appears in the above-identified patent and that said Letters Patent are hereby corrected as shown below:

On the first page, in the Abstract, [57], last line, "450°-640°C." should read --450°-650°C.--

Signed and Sealed this eighteenth Day of May 1976

[SEAL]

Attest:

RUTH C. MASON
*Attesting Officer*

C. MARSHALL DANN
*Commissioner of Patents and Trademarks*